US00PP10596P

United States Patent [19]

Kanno

[11] Patent Number: Plant 10,596

[45] Date of Patent: Sep. 8, 1998

[54] OSTEOSPERMUM PLANT NAMED 'BRIGHTSIDE'

[75] Inventor: Masao Kanno, Chigasaki, Japan

[73] Assignee: Sakata Seed America, Inc., Morgan Hill, Calif.

[21] Appl. No.: 707,927

[22] Filed: Sep. 10, 1996

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Melissa L. Kimball
*Attorney, Agent, or Firm*—James R. Cypher

[57] ABSTRACT

The present invention relates to a new and distinct variety of the Compositae family, *Osteospermum fruticosum* (L.) Norl., common name Cape Daisy, denominated 'Brightside.'

The new variety is distinguished from its parents and all other members of the genera known to the inventor by: the ability of its flower heads to remain open in low light conditions, its distinctive coloring — the ray florets being pure white and the disk florets being violet blue; its strong peduncles; and its dwarf, vigorous, broad-spreading growth habit.

1 Drawing Sheet

BACKGROUND OF THE INVENTION

The present invention relates to a new and distinct variety of the Compositae family. The new variety is named *Osteospermum fruticosum* (L.) Norl. 'Brightside'. A common name for the species to which the new variety belongs is Cape Daisy. The inventor is Mr. Masao Kanno, a Japanese citizen.

This new variety originated as a seedling from a controlled hybridization by the inventor. The starting material for the hybridization were *osteospermum fruticosum* (L.) Norl. 'Burgundy Purple' and *Osteospermum fruticosum* (L.) Norl. 'White', these two varieties being selected from the inventor's breeding stock in Japan. The objective of the breeding program was to develop a variety suitable for pot culture whose flower heads would reamin open under low light conditions. The species *Osteospermum fruticosum* (L.) Norl. normally only remains open in bright sunlight.

In 1986, the inventor crossed *Osteospermum fruticosum* (L.) Norl. 'Burgundy Purple' with *Osteospermum fruticosum* (L.) Norl. 'White'. From this first cross, the inventor selected two seedlings designated *Osteospermum fruticosum* (L.) Norl. 'Dwarf Pink' and *Osteospermum fruticosum* (L.) Norl. 'Dwarf White' for further development. 'Dwarf Pink' and 'Dwarf White' were selected for their compact growth habit. The inventor then crossed, the variety 'Dwarf Pink' with the parent 'Burgundy Purple', producing the seedling designated *Osteospermum fruticosum* (L.) Norl. 'No. 24'. The variety designated 'No. 24' possessed the desired characteristic: its flower heads did not close in late afternoon or under low light conditions. Variety 'No. 24' remained partially open even at night. In 1989, the inventor crossed 'No. 24' with 'Dwarf Pink' and 'No. 24' with 'Dwarf White'. Seedlings from these crosses ranged in habit from dwarf to tall. The color of the ray florets of these seedlings included burgundy purple, white, pink and bicolor varieties. Six seedlings from the crosses of 'Dwarf Pink' and 'Dwarf White' with 'No. 24' were selected for further investigation and were propagated by self-pollination. In the spring of 1990, the inventor propagated the six selected varieties by cuttings to determine if the color and other characteristics where fixed. Four varieties were determined to have fixed distinguishing characteristics after asexual propagation, one of which is the new cultivar described herein named 'Brightside.' The controlled hybridization was conducted at the Sakata Seed Chogo Research Station, 2633 Kamiyadai Chogo, Fujisawa City, Kanagawa Prefecture 252, Japan, under usual commercial nursery conditions.

The new variety is particularly suitable for commercial pot culture because of its strong peduncles; dwarf, spreading, compact growing habit; all day blooming habit; profusion of flower heads; and long blooming season (recurrent the year round at Salinas, Calif.).

The characteristics of the new variety which in combination distinguish it from its parents and all other varieties known to the inventor are: the ability of its flower heads to remain open in low light conditions; its distinctive coloring — the upper sides of the petals of the ray florets being pure white and the disk florets being R.H.S. 90C Violet-Blue Group; its strong peduncles; and its dwarf, vigorous, broad-spreading growth habit.

The distinguishing characteristics are retained through successive generations when asexually reproduced by vegetative cuttings of terminal shoots. Since the inventor's discovery and initial asexual propagation of the new variety in Japan, the assignee, under the direction and control of the inventor, has also asexually reproduced the new variety through successive generations by means of cuttings at its commercial nursery in Salinas, Calif., and has found that the combination of characteristics as herein disclosed remain firmly fixed.

The following table compares the new variety to the closest varieties known to the inventor. These are *Osteospermum fruticosum* (L.) Norl. 'White', *Osteospermum fruticosum* (L.) Norl. 'Dwarf White', and *Osteospermum fruticosum* (L.) Norl. 'Merite'.

| | New cultivar 'Brightside' | 'Merite' | 'Dwarf White' | 'White' |
|---|---|---|---|---|
| Response to low light conditions | flower heads remain open | flower heads close | flower heads close | flower heads close |
| Color of mature ray florets (upper side) | pure white | off white | white | white |

-continued

| | New cultivar 'Brightside' | 'Merite' | 'Dwarf White' | 'White' |
|---|---|---|---|---|
| Growth habit of peduncles. | strong | weak | weak | strong |
| General growth habit. | dwarf, vigorous, broad | semi-dwarf, vigorous, medium | dwarf, vigorous, broad | tall and narrow |

The following table compares the new variety with the selected members of its generation of the inventor's hybridization along selected distinguishing characteristics:

| | New cultivar 'Brightside' U.S. S/N: 08/707,927 | New cultivar 'Seaside' U.S. S/N: 08/707,928 | New cultivar 'Highside' U.S. S/N: 08/707,926 | New cultivar 'Wildside' U.S. S/N: 08/711,481 |
|---|---|---|---|---|
| Color of mature ray florets (upper side) | pure white | Tips: R.H.S. 73B Base: R.H.S. 155C | R.H.S. 72B | R.H.S. 71A |
| Color of disk florets | R.H.S. 90C | R.H.S. 89C | R.H.S. 89C | R.H.S. 90C |
| General growth habit. | dwarf, vigorous, broad spreading | dwarf, vigorous, broad spreading | dwarf, vigorous, medium spreading | dwarf, vigorous, medium spreading |

BRIEF DESCRIPTION OF THE DRAWINGS

The new variety of *Osteospermum fruticosum* (L.) Norl. is illustrated by the accompanying color photographs which show the potted plant form, growth habit, inflorescence, foliage, and color characteristics of the plant. The colors are represented as truly as possible using conventional photographic procedures.

DETAILED DESCRIPTION OF THE NEW VARIETY

Figure 1:
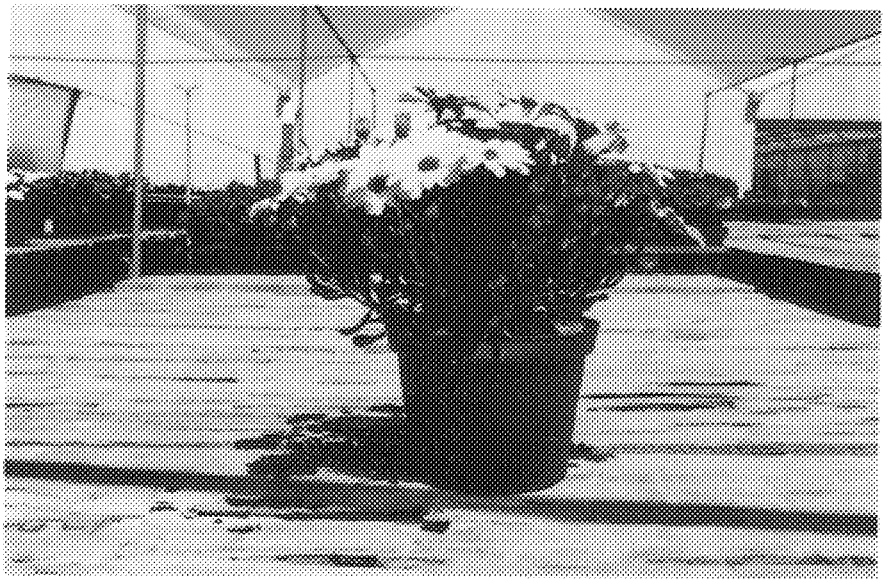
FIG. 1 is a front perspective view of a potted plant of the new variety as described herein, illustrating the overall form and appearance of the plant in full bloom.
Figure 2:
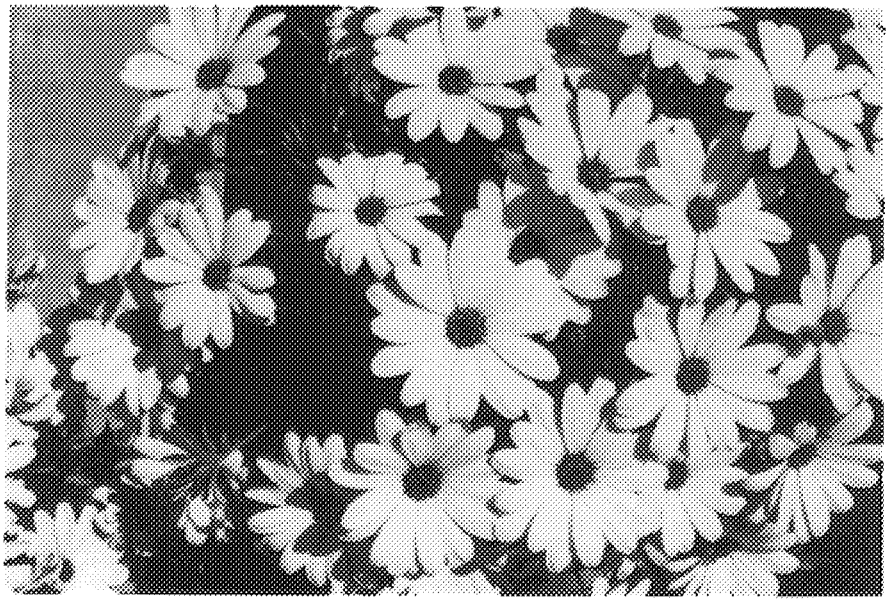
FIG. 2 is a close-up view of the inflorescence of the plant.

The following is a detailed description of the new variety. Color designations were made according to the R.H.S. Color Chart published by The Royal Horticultural Society of London, England.

Observed plants were grown outdoors in Salinas, Calif. where the night temperature ranges on average from 50° to 60° Fahrenheit, and the average daytime temperature ranges from 65° to 70° Fahrenheit. Cuttings were put into 6" pots in early August. 3 cuttings were put in each pot. Buds were pinched in December. Flowers bloomed in June of the following year.

The Plant

Origin: Seedling.

Parentage: *Osteospermum fruticosum* 'No. 24' and either *Osteospermum fruticosum* 'Dwarf Pink' or *Osteospermum fruticosum* 'Dwarf White'.

Classification:

*Botanic.*—Family — Compositae. Species — *osteospermum fruticosum* (L.) Norl.

*Commercial common name.*—Cape Daisy.

*Cultivar name.*—'Brightside'.

Form: Upright, compact, perennial shrub.

Height: As much as 36 cm. to 46 cm. for potted plants under optimum growing conditions.

Growth: Dwarf, broad-spreading, mounded, vigorous, well-branched, self-branching.

Foliage:

*Stems.*—Strong, stiff peduncles, caulescent, herbaceous, ascending, erect, glabrous.

*Leaves.*—Simple spatulate, pinnatifid, denticulate, alternate, entire, with netted veins, rarely opposite, color is R.H.S. 137A Green Group on both top and bottom of leaves, variable in size, average 6.4 cm. long by 2.5 cm. wide.

Flower heads:

*Buds.*—Buds are various shades of yellow.

*Flower heads.*—Solitary on terminal peduncles.

*Bracts.*—Radiate involucral bracts in 1–3 rows.

*Receptacle.*—Flat or convex, naked.

*Receptacle diameter.*—8 mm.

*Disk florets.*—Tubular, male, anthers, sagittate, color is R.H.S. 90C Violet-Blue Group, pollen color is R.H.S. 23B Yellow-Orange Group.

*Ray florets.*—Ligulate, female, upper side of the petals is pure white. The lower side of the petals are various shades of blue-white. As the florets age, the lower sides of the petals develop a white margin.

*Achenes.*—All alike or dimorphic or rarely even polymorphic.

*Flower head diameter.*—7.5 cm (petal tip to petal tip).

*Response to low light conditions.*—Flower heads remain open with petals of ray florets remaining reflexed.

Bloom period: Plants bloom continuously outdoors under normal climate conditions at Salinas, Calif. Individual flower heads last 3–7 days outdoors. Plants grown in greenhouses bloom for about two weeks at a time.

Frost resistance: High.

Disease resistance: Unknown.

Fragrance: None.

I claim:

1. A new and distinct hybrid plant variety of the Compositae family, *Osteospermum fruticosum* (L.) Norl., common commercial name Cape Daisy, named 'Brightside' substantially as herein shown and described.

* * * * *